(12) United States Patent
Richmond

(10) Patent No.: US 8,534,302 B2
(45) Date of Patent: Sep. 17, 2013

(54) PROBER CLEANING BLOCK ASSEMBLY

(75) Inventor: Robert A. Richmond, Maricopa, AZ (US)

(73) Assignee: Microchip Technology Incorporated, Chandler, AZ (US)

( * ) Notice: Subject to any disclaimer, the term of this patent is extended or adjusted under 35 U.S.C. 154(b) by 1036 days.

(21) Appl. No.: 12/560,817

(22) Filed: Sep. 16, 2009

(65) Prior Publication Data

US 2010/0139716 A1 Jun. 10, 2010

Related U.S. Application Data

(60) Provisional application No. 61/121,012, filed on Dec. 9, 2008.

(51) Int. Cl.
*B08B 3/00* (2006.01)

(52) U.S. Cl.
USPC ............. 134/135; 134/1.2; 134/1.3; 134/902; 324/758.01

(58) Field of Classification Search
USPC .......... 134/1.2, 1.3, 6, 135, 902; 324/754.03, 324/754.07, 758.01
See application file for complete search history.

(56) References Cited

U.S. PATENT DOCUMENTS

| | | | |
|---|---|---|---|
| 5,804,983 A | 9/1998 | Nakajima et al. | 324/758 |
| 5,968,282 A * | 10/1999 | Yamasaka | 134/6 |
| 6,111,421 A | 8/2000 | Takahashi et al. | 324/758 |
| 6,118,289 A * | 9/2000 | Kitani et al. | 324/754.03 |
| 6,777,966 B1 * | 8/2004 | Humphrey et al. | 324/754.07 |
| 6,813,804 B2 | 11/2004 | Kim et al. | 15/306.1 |
| 7,202,683 B2 * | 4/2007 | Humphrey et al. | 324/758.01 |
| 7,345,466 B2 | 3/2008 | Vogtmann et al. | 324/758.04 |
| 2003/0200989 A1 * | 10/2003 | Humphrey et al. | 134/2 |
| 2003/0206031 A1 | 11/2003 | Harris | 324/758 |
| 2004/0083568 A1 * | 5/2004 | Morioka et al. | 15/118 |
| 2004/0227532 A1 | 11/2004 | Orsillo | 324/754 |

FOREIGN PATENT DOCUMENTS

| | | |
|---|---|---|
| CN | 1466182 A | 1/2004 |
| CN | 101238380 A | 8/2008 |
| CN | 101249630 A | 8/2008 |
| EP | 0 260 024 | 3/1988 |
| GB | 2 316 536 A | 2/1998 |
| WO | 2004/010153 A2 | 1/2004 |
| WO | 2007/016599 A1 | 2/2007 |

OTHER PUBLICATIONS

International PCT Search Report and Written Opinion, PCT/US2009/067341, 17 pages, mailed Apr. 21, 2010.
Chinese Office Action, Application No. 200980148831.0, 19 pages, Mar. 25, 2013.

* cited by examiner

*Primary Examiner* — Michael Kornakov
*Assistant Examiner* — Benjamin L Osterhout
(74) *Attorney, Agent, or Firm* — King & Spalding L.L.P.

(57) ABSTRACT

A system is provided for cleaning of probe contacts. The system has a base plate with three mounting means, such as openings, for receiving each an adjustable attachment, and means, such as further openings, for connecting the base plate to a probe machine; and a cleaning plate having on a bottom side three holding means, such as openings, for receiving the respective adjustable attachment, and a top area for supporting a cleaning device, wherein the holding means do not reach into a top area of the cleaning plate; and wherein the adjustable attachment means allows the top area to be leveled.

20 Claims, 5 Drawing Sheets

PROBER CLEANING BLOCK ASSEMBLY

CROSS-REFERENCE TO RELATED APPLICATIONS

This application claims the benefit of U.S. Provisional Application No. 61/121,012 filed on Dec. 9, 2008, entitled "PROBER CLEANING BLOCK ASSEMBLY", which is incorporated herein in its entirety.

TECHNICAL FIELD

The technical field of the present invention relates to cleaning of a probe in a wafer probing machine. More particularly, the present invention relates to a system for cleaning contacts of a probe and a method for mounting a cleaning plate for a probe in a probe machine.

BACKGROUND

In recent years, attention has been given to cleaning of probes, especially in the field of semiconductor (IC) fabrication. In conventional semiconductor fabrication, wafers, prior to being cut into individual chips, are tested by a probe, also known as probe card, to evaluate if the function of the semiconductor chips thereon is normal. During testing, a plurality of probe needles or pins of the probe physically contact the testing pads on the wafer under test to measure the electrical properties of semiconductor devices formed on the wafer. For inspection in a wafer probing machine, the wafer is placed on the main chuck, which is movable in the X, Y, Z and θ directions. The wafer is index-fed by moving the main chuck. The probe pins or needles of the probe card are brought into contact with the electrode pads of the chips on the wafer that is being index-fed during inspection. The electrodes of the chips are electrically connected to a tester, so as to inspect the electric characteristics of the chips.

However, after long use and in order to achieve reliable electric connection between the probe needles and the electrode pads, the probe needle tips are usually contaminated by various metal particles and their oxides. This influences the accuracy of the testing results during testing and lowers the test quality. The probe card is therefore cleaned to remove the residue on the probe tips after long use.

The tip ends of a plurality of probe needles may be supported on a probe card at one end. The probe needles are arranged in such a manner that they can simultaneously be brought into contact with the electrodes on the chips. A probe needle array can cover a large area and 400 to 500 probe needles may be present. It is desirable that a cleaning unit for the probe achieves to clean existing and future probe card arrays.

It is further desirable to clean these probe needles efficiently and safely. Additionally, such probe needle tips must maintain the same level. The array of probe needles should desirably be in the same level as a cleaning block when the needles are cleaned. If a probe would be cleaned irregularly, then the probe needle tips may not contact the chip properly and the test result would be influenced.

The moving range of the wafer chuck also put its restriction on how the cleaning may be performed. The available space within a wafer probing machine also restricts the cleaning. It is desirable that a cleaning system physically fit in a probe machine, such as for example the UF200 or the APM90, without interfering with adjacent mechanical components and/or control software. Consequently, there is a need to consider the shape and size of the available space in a probe machine and/or the requirements set by a probe, such as for example smoothness and level.

Additionally, it is always desirable to speed up the processing time, for example probe die yields, of a probe machine. A decrease in probe testing time is preferred, especially in existing cleaning units. For example, existing methods and/or machines call for a product wafer to be offloaded and then a cleaning wafer loaded onto the wafer chuck. Then the cleaning is performed by the probe card engaging the needles of the probe card with the cleaning wafer. Hereafter, the product wafer must be reloaded, followed by a sufficient time for the wafer to heat up to process temperature, and then the probing may resume. Increase in the needle or probe tip cleaning frequency without increasing test times is desirable.

SUMMARY

According to one embodiment a system for cleaning probe contacts may include a base plate and a cleaning plate. The base plate may include three mounting means for receiving each an adjustable attachment means, and means for connecting the base plate to a probe machine. The cleaning plate may include three holding means for receiving the respective adjustable attachment means, and a top area for cleaning probe contacts. Preferably the top area is between 60-100 mm times 75-100 mm, and the adjustable attachment means allows the cleaning plate to be leveled.

According to one embodiment a method for mounting in a probe machine a system for cleaning probe contacts may be provided. The system may include a base plate comprising three mounting means for receiving each an adjustable attachment means, and means for connecting the base plate to a probe machine; and a cleaning plate comprising three holding means for receiving the respective adjustable attachment means, and a top area for cleaning probe contacts; wherein the top area is between 60-100 mm times 75-100 mm, and the adjustable attachment means allows the cleaning plate to be leveled. The first step of the method may be connecting the base plate in the probe machine. The second step of the method may be connecting the cleaning plate to the base plate with the adjustable attachment means by mounting one of the adjustable attachment means as a reference, and mounting the two other adjustable attachment means for adjusting the level of the cleaning plate. The third step of the method may be leveling, with the aid of measuring means for measuring distance held by the probe machine, the cleaning plate by repeating the following steps until the desired level is reached: moving the measuring means to a place on the cleaning plate top area that is substantially above the adjustable attachment means used as a reference and measure a reference value with the measuring means; moving the measuring means to a place on the cleaning plate top area that is substantially above one of the two adjustable attachment means for adjusting the level and adjust that attachment means until the measuring means reads substantially the same as the reference value; and moving the measuring means to a place on the cleaning plate top area that is substantially above the other of the two adjustable attachment means for adjusting the level and adjust that attachment means until the measuring means reads substantially the same as the reference value.

At least one of the embodiments may provide a system for cleaning large probe arrays. At least one of the embodiments may provide a method for mounting in a probe machine a system for cleaning large probe arrays. Such a system and method may achieve to clean existing and future probe card arrays of a large size, for example probe cards having several hundreds of probe needles.

At least one of the embodiments may clean these probe needles efficiently and safely and/or maintain the same level when cleaning the probe contacts. Such embodiments may assure proper contact between the probe contacts and the chip and therefore not influence the test result.

At least one of the embodiments may allow cleaning to be performed in probe machines, such as for example the UF200 or the APM90, without interfering with adjacent mechanical components and/or control software. Such embodiments may consider the shape and size of the available space in a probe machine and/or the requirements set by a probe, such as for example smoothness and level.

At least one embodiment may improve overall probe die yields by reducing probe contact resistance without increasing probe processing test time per wafer. As a result, specific device cleaning requirements may reduce testing time on many products.

At least one embodiment allows gains in probe die yields by arranging the cleaning system adjacent to the wafer chuck in the probe machine. Hereby the X/Y stage need only move a short distance when the programmed cleaning interval is initiated to position the cleaning block to engage and clean the probe card needles, thus lowering contact resistance.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiment(s).

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain, by way of example, the principles of the invention.

DETAILED DESCRIPTION

Preferred embodiments and their advantages are best understood by reference to FIGS. 1 to 7, wherein like numbers are used to indicate like and corresponding parts. A wafer probing machine may test electric characteristics of one or more chips created on a wafer. The test is made by probe contacts of a wafer prober contacting each chip of a wafer on the wafer chuck of a wafer probe machine. By this testing, chips are sorted into good or defective chips. The hereinafter described exemplary system may be used for cleaning such probe contacts and the hereinafter described exemplary method may be used for mounting in a probe machine such a system for cleaning of probe contacts.

Figure 1:
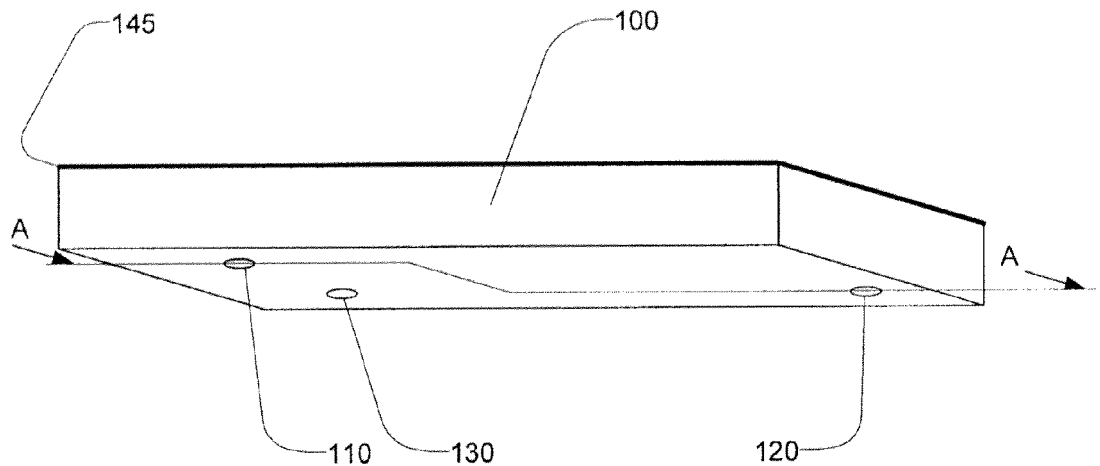
FIG. 1 illustrates an example of an embodiment of a cleaning plate.

FIG. 1 illustrates an exemplary embodiment of a cleaning plate 100. The cleaning plate 100 comprises three holding means in the preferred shape of three blind threaded holes 110, 120, and 130. The cleaning plate 100 may be substantially rectangular. One holding means 110 is situated approximately in one of the four corners of the cleaning plate 100, for example at the front left hand corner as indicated in FIG. 1. One holding means 120 is situated approximately in one of the other three corners of the cleaning plate 100, for example at the rear right hand corner as indicated in FIG. 1. One holding means 130 is situated approximately in one of the other two corners of the cleaning plate 100, for example at the rear left hand corner as indicated in FIG. 1. In this way each holding means may be located in a respective corner of the cleaning plate 100 and located such that they form a triangular basis for holding and supporting the cleaning plate 100. The holding means may be two or four in numbers, but the preferred embodiment has three.

Figure 6:
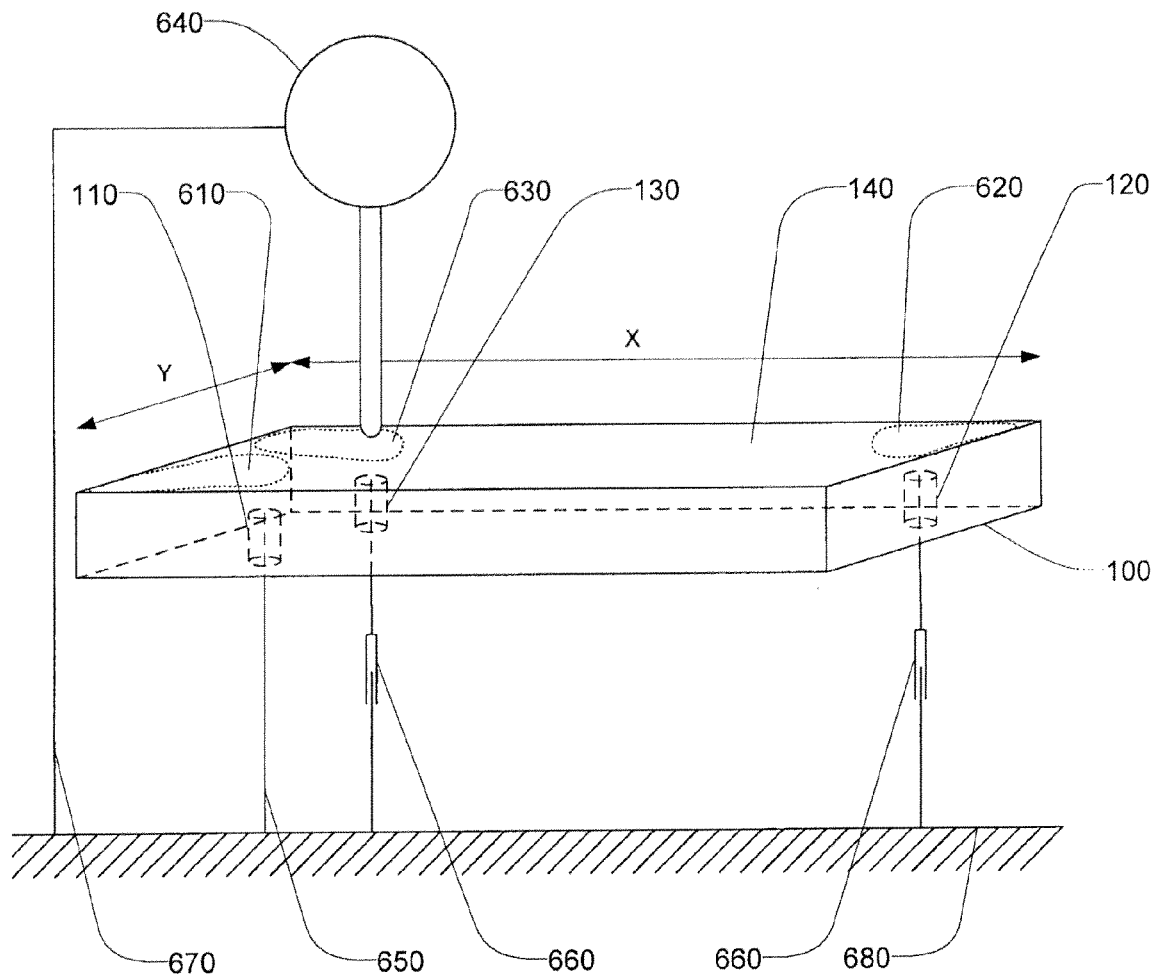
FIG. 6 illustrates measuring means engaging the cleaning plate illustrated in FIG. 1.

According to one embodiment, the cleaning plate 100 has a top area 140 as illustrated in FIG. 6. The rectangular size of the top area 140 is illustrated with the letters X and Y. X may be between 50 and 150 mm and Y may be between 50 and 150 mm. Preferably, X may be between 60 and 100 mm and Y may be between 75 and 100 mm. According to one embodiment, for a specific probe machine, such as for example a UF200, X may be 100 mm and Y may be 100 mm. According to another embodiment, for a specific probe machine, such as for example an APM90, X may be 95 mm and Y may be 60 mm. These rectangular sizes allows the cleaning plate 100 to effectively clean large probe arrays, for example probe arrays with 400 to 500 or more probe needles, while not interfering with components of a probe machine.

Figure 2:
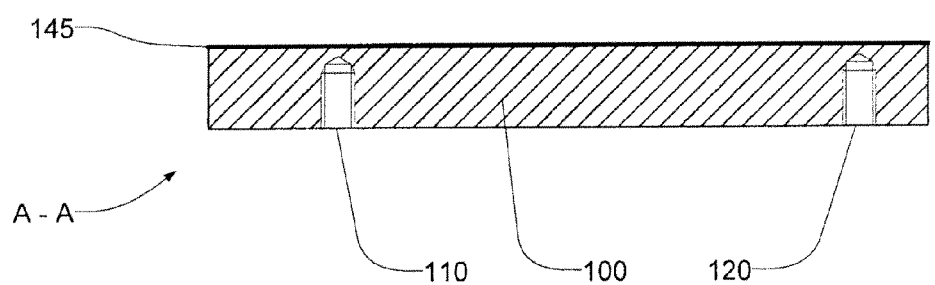
FIG. 2 illustrates a view along line A-A in FIG. 1.
Figure 5:
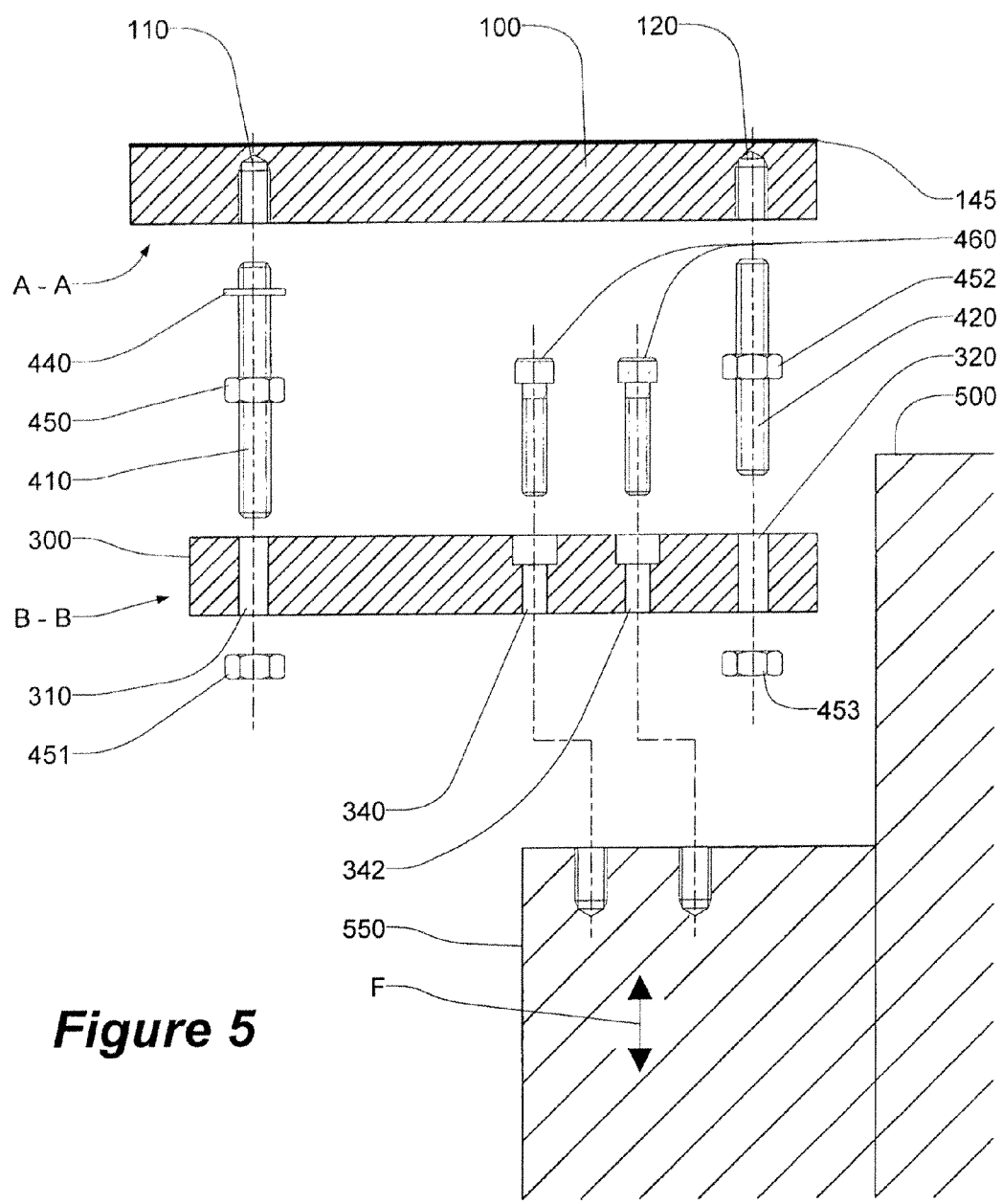
FIG. 5 illustrates an exemplary embodiment of the views of FIGS. 2 and 4 and how they may be mounted to a probe machine.

According to one embodiment, the top area 140 may be covered with a cleaning film 145. This cleaning film 145 is illustrated in FIGS. 1, 2 and 5; however not in FIG. 6 because here the cleaning plate 100 is illustrated in the process of being leveled by a measuring means 640 engaging the top area 140. The cleaning film 145 may be attached to the cleaning plate 100 after the cleaning plate 100 has been installed and leveled to avoid damaging the cleaning film 145. The cleaning film may preferably be ITS Probe Scrub™. Instead of the cleaning film 145 a tungsten carbide layer may be used. The cleaning film 145 may cover the whole top area 140 on the side of the cleaning plate that is opposite the side comprising the holding means 110, 120, and 130.

Turning to FIG. 2, a view along line A-A in FIG. 1 is illustrated. The holding means 110 may be situated in the direction of, or an area approximately close to, the front left hand corner of the cleaning plate 100. The holding means 120 may be situated in the direction of, or an area approximately close to, the rear right hand corner of the cleaning plate 100. The holding means 130, not shown in the view A-A, may be situated in the direction of, or an area approximately close to, the rear left hand corner of the cleaning plate 100. These holding means has been illustrated as blind threaded holes, but may be any suitable means for holding the cleaning plate 100.

Figure 3:
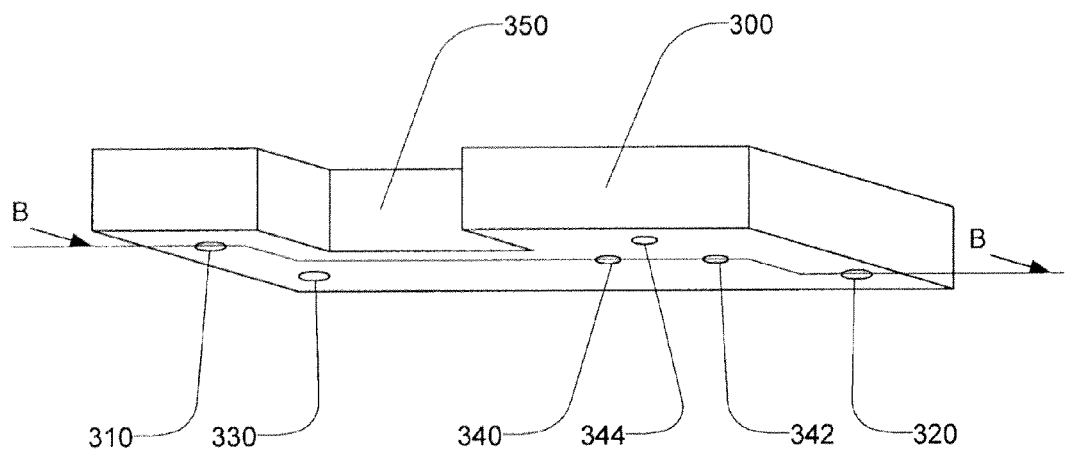
FIG. 3 illustrates an example of an embodiment of a base plate.
Figure 4:
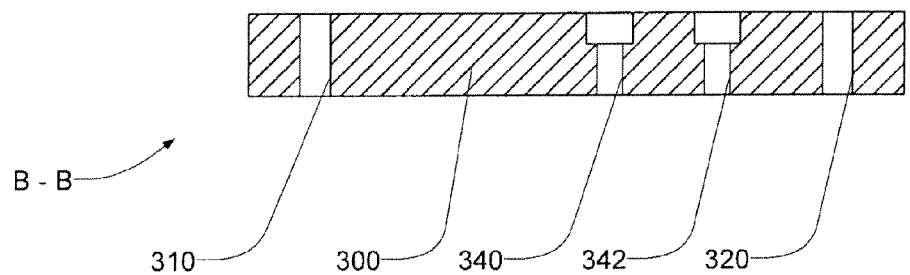
FIG. 4 illustrates a view along line B-B in FIG. 3.

Turning to FIGS. 3 and 4, a base plate 300 is illustrated. The base plate 300 comprises mounting means 310, 320, and 330 for receiving adjustable attachment means for connecting the base plate 300 with the cleaning plate 100, and means 340, 342, and 344 for connecting the base plate 300 to a probe machine.

FIG. 3 illustrates an example of an embodiment of the base plate 300. The base plate 300 may have three mounting means in the preferred shape of openings 310, 320, and 330 corresponding to the three holding means in the preferred shape of three blind threaded holes 110, 120, and 130 of the cleaning plate 100. These mounting means allows for adjustable attachment means to connect the base plate 300 with the cleaning plate 100. The mounting means may be two or four in numbers, or any other suitable numbers, but the preferred embodiment has three.

Additionally, the base plate 300 may have means for connecting the base plate 300 to a probe machine. According to one embodiment, the means 340, 342, and 344 for connecting the base plate 300 to a probe machine may be counter bored holes 340, 342, and 344 for allenhead cap screws. Hereby the base plate 300 may be connected to a part, for example to a mount close to or on a wafer chuck, of a probe machine. The means for connecting may be two or four in numbers, but the preferred embodiment has three. The means 340, 342, and 344 for connecting the base plate 300 to a probe machine may be orientated in the corners of a triangular shape to allow for holding and supporting the base plate 300 securely.

According to one embodiment, the base plate 300 may have one or more passages 350. Such a passage 350 may allow parts of the probe machine not to interfere with the base plate 300 supporting the cleaning plate 100. For example, a camera leadscrew of the probe machine may be allowed to enter such a passage 350.

FIG. 4 illustrates a view along line B-B in FIG. 3. The mounting means 310 may be situated in the direction of, or an area approximately close to, the front left hand corner of the base plate 300. The mounting means 320 may be situated in the direction of, or an area approximately close to, the rear right hand corner of the base plate 300. The mounting means 330, not shown in the view B-B, may be situated in the direction of, or an area approximately close to, the rear left hand corner of the base plate 300. These mounting means have been illustrated as holes; however any means for receiving attachment means for connecting the base plate 300 with the cleaning plate 100 may be used.

According to one embodiment, the system for cleaning probe contacts may be mounted as illustrated in FIG. 5. Here the exemplary embodiments illustrated in the views of FIGS. 2 and 4 are mounted on a motor controlled mounting frame 550, which in turn may be mounted on a wafer chuck 500 in a probe machine. The mounting frame 550 may be movable in the Z direction, independently of the usual directions X, Y, Z, and θ of the wafer chuck. This up and down movement of the mounting frame 550 may be referred to as the F direction and has been illustrated with a double arrow indicated with letter F in FIG. 5. The mounting frame 550 may for example be a mounting flange and movable in the F direction independently from the Z movement of the wafer chuck.

According to one embodiment, the base plate 300 may be connected to the mounting frame 550 by means of, for example three cap screws 460. Two of these cap screws 460 have been illustrated in FIG. 5. Hereby the base plate 300 may be mounted in the probe machine and allows for the cleaning plate 100 to be supported on the base plate 300 and leveled with respect to the probe machine, for example with respect to the wafer chuck 500 or a probe within the probe machine. The screws 460 may each have a washer, preferably a split washer, to lock the screws securely.

According to one embodiment, the cleaning plate 100 is connected to the base plate 300 by adjustable attachment means. The adjustable attachment means may be three screws of which two screws 410 and 420 have been illustrated in FIG. 5. The third screw is identical with screw 420 and has therefore been omitted. Each of the three screws may have two nuts 450, 451, 452, and 453.

Screw 410 may be threaded into the blind threaded hole 110; subsequently a first nut 450 may be threaded onto the screw, followed by the mounting means 310 of the base plate 300, followed by a second nut 451. In this way the cleaning plate 100 may be connected to the base plate 300. This adjustment means may be referred to as the reference point. A washer 440, preferably a split washer, may be additionally mounted onto the screw 410 between the cleaning plate 100 and the base plate 300. The washer 440 may be mounted on either side of the first nut 450. This washer 440 assures that the other two adjustment means may be adjusted in the Z direction, even if all nuts have the same thickness. In other words, the washer 440 ensures that a gap between the base plate 300 and the cleaning plate 100 at the front left corner (the reference point) will not interfere with a gap and leveling at the two back corners. If the nut 450 at the front left reference position would be thinner then the two nuts at the back positions, it may prevent an operator from being able to set the proper level of the cleaning plate 100.

The second screw 420 may be threaded into the blind threaded hole 120; subsequently a first nut 452 may be threaded onto the screw, followed by the mounting means 320 of the base plate 300, followed by a second nut 453. The third screw that connects the blind threaded hole 130 with the mounting means 330 has been omitted because it is identical to the second screw 420. The third screw may be threaded into the blind threaded hole 130, subsequently a first nut may be threaded onto the screw, followed by the mounting means 330 of the base plate 300, followed by a second nut. In this way the cleaning plate 100 may be connected to the base plate 300.

Figure 7:
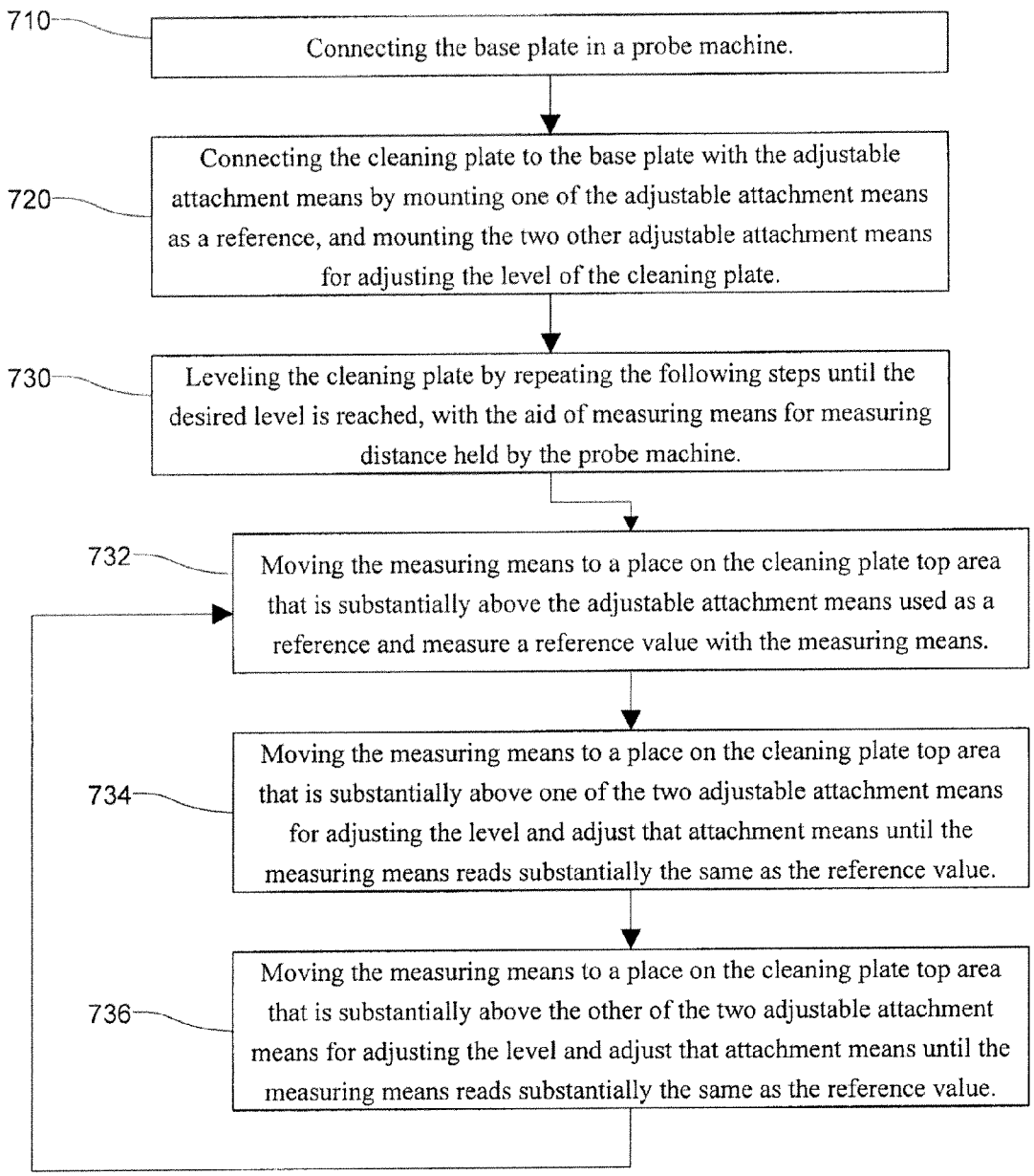
FIG. 7 illustrates a flow chart of an exemplary method of an embodiment.

Turning to FIGS. 6 and 7, a method for mounting in a probe machine a system for cleaning of probe contacts is illustrated, especially how to level the cleaning plate 100 with respect to the probe machine. The larger a cleaning plate is made, the more important and the more difficult, if not impossible, it becomes to level that cleaning plate so that proper cleaning of all contact needles may be performed. Similar, a cleaning plate can simply not be made arbitrary large because of the physical limitations within the probe machine in which it must be placed.

FIG. 6 illustrates measuring means 640 engaging the cleaning plate 100 illustrated in FIG. 1. The measuring means 640 may for example be a dial indicator or any other type of measuring means capable of measuring linear displacement. In an attempt to disclose by example the basic principles as clearly as possible of mounting and leveling the cleaning plate 100, the three adjustment means have been schematically illustrated as one adjustable attachment 650 that has been fixed and two adjustable attachment means 660 that allows for adjustment. The adjustable attachment 650 that has been fixed connects the holding means 110 to the probe machine via the base plate 300, which has been omitted in FIG. 6 for the sake of clarity. The two adjustable attachment 660 that allows for adjustment connect the holding means 120 and 130, respectively, to the probe machine via the base plate 300, which has been omitted in FIG. 6 for the sake of clarity.

The measuring means 640 may be connected via suitable means, indicated schematically as reference number 670 in FIG. 6, to a probe machine 680 in which the cleaning plate 100 is installed. Hereby the measuring means 640 may measure the distance in the Z direction that different areas of the cleaning plate have with respect to the probe machine, or part of the probe machine such as for example the wafer chuck.

On the top area 140 of the cleaning plate 100 above the holding means 110 an area 610 has been marked. The area 610 may be referred to as the reference area 610, because this area may be used as a reference for leveling the cleaning plate 100. The area 610 may be the area substantially above the holding means 110 of the top area 140. The area 610 may be substantially equal to the corner corresponding to the holding means 110 of the cleaning plate 100. As an example, the area 610 may be about 1 to 5 times the corresponding area that the holding means 110 takes, for example as a blind hole. The measuring means 640 may be placed on the area 610 to set a reference value, for example zeroing the measuring means.

On the top area 140 of the cleaning plate 100 above the holding means 120 an area 620 has been marked. The area 620 may be the area substantially above the holding means 120 of the top area 140. The area 620 may be substantially equal to the corner corresponding to the holding means 120 of the cleaning plate 100. As an example, the area 620 may be about 1 to 5 times the corresponding area that the holding means 120 takes when being blind holes. As an other example, the area 620 may be substantially a corner area suitable for, and at least large enough for, engaging the measuring means 640 with the area 620. The measuring means 640 may be moved to engage the area 620 to measure the distance (in the Z direction) that the area 620 is off set from the reference area 610. Hereby a value is given of the amount that the adjustment means 660 connected to the holding means 120 should be adjusted to level the cleaning plate 100. In this way the area 620 may be brought to the same level (in the Z direction) as the reference area 610. More specifically, the distance between the area 620 and the corresponding corner of the base plate may be adjusted.

On the top area 140 of the cleaning plate 100 above the holding means 130 an area 630 has been marked. The area 630 may be the area substantially above the holding means 130 of the top area 140. As an example, the area 630 may be about 1 to 5 times the corresponding area that the holding means 130 takes, for example as a blind hole. As an other example, the area 630 may be substantially a corner area suitable for, and at least large enough for, engaging the measuring means 640 with the area 630. The measuring means 640 may be placed on the area 630 to measure the distance (in the Z direction) that the area 630 is off set from the reference area 610. Hereby a value is given of the amount that the adjustment means 660 connected to the holding means 130 should be adjusted to level the cleaning plate 100. The area 630 may be brought to the same level (in the Z direction) as the reference area 610. More specifically, the distance between the area 630 and the corresponding corner of the base plate may be adjusted.

According to at least one embodiment, the cleaning plate 100 may be leveled by measuring a reference value, or setting the measuring means 640 to zero when engaging, for example, the area 610 and subsequently adjusting the other two areas 620 and 630 to the same level using the measuring means 640. Hereafter, the measuring means 640 may measure a new reference value, or setting the measuring means 640 again to zero when engaging the reference area 610 and subsequently adjusting the other two areas 620 and 630 to the same level again using the measuring means 640. This may be repeated until the measuring means 640 may indicate that the areas 610, 620, and 630 have the same level, or are within the required level tolerance. According to an embodiment, the level of the cleaning plate 100 is required to be less than 15 μm. In other words, the difference between the areas 610, 620, and 630 may be less than 15 μm. Alternatively, one of the areas 620 or 630 could be used as reference area and the other two areas may be adjusted accordingly. In an embodiment with more or less than three adjustment means, any area may be used as the reference area while the remaining areas may be adjusted.

FIG. 7 illustrates a flow chart of an exemplary method 700 of an embodiment for mounting in a probe machine a system for cleaning of probe contacts. According to one embodiment, method 700 preferably begins at step 710. As noted above, teachings of the present disclosure may be implemented in a variety of configurations of the system. As such, the preferred initialization point for method 700 and the order of the steps 710 to 730 may depend on the implementation chosen. At step 730 the leveling may be performed by the three steps 732, 734, and 736. The three steps 732, 734, and 736 may be taken in any order resulting in leveling and step 732 may be repeated in between the other two steps 734 and 736. Example of orders of the steps may be: 732, 736, and 734; or 732, 734, 732, and 736.

According to one embodiment, the method 700 is for mounting in a probe machine the system for cleaning of probe contacts described above or any other suitable system. Such a system may comprise a base plate comprising three mounting means for receiving each an adjustable attachment means, and means for connecting the base plate to a probe machine; and a cleaning plate comprising three holding means for receiving the respective adjustable attachment means, and a top area for cleaning probe contacts. Further, the top area may be between 60-100 mm times 75-100 mm, and the adjustable attachment means allows the cleaning plate to be leveled with respect to the probe machine, preferably a wafer chuck within the probe machine.

At step 710, the base plate may be connected to a probe machine. According to an embodiment, the base plate may be mounted on a mounting frame, which in turn may be mounted on a wafer chuck in a probe machine. The mounting may be effected by means of, for example three cap screws, connecting the base plate to the mounting frame. Hereby the base plate may be mounted in the probe machine and allows for the cleaning plate to be supported on the base plate and leveled with respect to the probe machine, for example with respect to the wafer chuck or a probe within the probe machine.

At step 720, the cleaning plate may be connected to the base plate. According to an embodiment, connecting the cleaning plate to the base plate with the adjustable attachment means may be done by mounting one of the adjustable attachment means as a reference, and mounting the two other adjustable attachment means for adjusting the level of the cleaning plate. Hereby the cleaning plate may be leveled and connected to the base plate.

At step 730, the cleaning plate is leveled, preferably with reference to the probecard holder tray in the probe machine. According to an embodiment, leveling the cleaning plate may be done by repeating the following steps 732, 734, and 736 until the desired level is reached. The step 732 may also be performed in between the two subsequent steps 734 and 736. The leveling may be done with the aid of measuring means for measuring distance held by the probe machine. Such measuring means may for example be a dial indicator.

At step 732, the measuring means may be used to create a reference value, for example by zeroing the measuring means, at substantially one corner of the cleaning plate, preferably the reference area as mentioned above. According to an embodiment, the measuring means may be moved to a place on the cleaning plate top area that is substantially above the adjustable attachment means used as a reference and measure a reference value with the measuring means. Hereby a reference value may be created that can be used for setting the other adjustable measuring means. This step 732 may also be performed in between the two subsequent steps 734 and 736.

At step 734, the measuring means may be moved to substantially one other corner of the cleaning plate and that corner may be adjusted with reference to the reference value. According to an embodiment, the measuring means may be moved to a place on the cleaning plate top area that is substantially above one of the two adjustable attachment means for adjusting the level and adjust that attachment means until the measuring means reads substantially the same as the reference value. Hereby the cleaning plate may be leveled.

At step 736, the measuring means may be moved to substantially a further corner of the cleaning plate and that corner may be adjusted with reference to the reference value. According to an embodiment, the measuring means may be moved to a place on the cleaning plate top area that is substantially above the other of the two adjustable attachment means for adjusting the level and adjust that attachment means until the measuring means reads substantially the same as the reference value. Hereby the cleaning plate may be leveled.

According to one embodiment, the adjustable attachment means may comprise three screws and two nuts for each screw and the adjustments are made by turning the nuts. This may allow for the cleaning plate to be adjusted to any desired distance from the base plate.

According to one embodiment, the cleaning plate may be mounted in a UF200 or a APM90 wafer probe machine. This may allow for a high die yield for large probe arrays in such machines.

According to one embodiment, the method may further comprise the step of initially cooling the chuck in the probe machine and allowing the machine to stabilize. Preferably the chuck is cooled to 30 degrees Celsius and the machine allowed to stabilize for 30 minutes. Hereby the mounting of the system and the leveling of the cleaning plate may not be adversely effected by temperature differences within the probe machine.

According to one embodiment, the leveling may be made to an accuracy of 5 μm. At least one embodiment of the system described above allows for such a high degree of level. With a level of at least 15 μm large contact arrays of probes may be cleaned.

According to one embodiment, the measuring means may be a dial indicator. Any measuring means capable of measuring distance may be used, and a dial indicator is only a preferred measuring means.

According to one embodiment, a washer may be placed on the screw used as reference point between the cleaning plate and the base plate. This washer separates the cleaning plate from the base plate at one of the corners more than the other corners. Hereby the other corners allow the cleaning plate to be leveled.

According to one embodiment, the method may further comprise, after the cleaning plate has been leveled, a step of applying a cleaning film to the cleaning plate. By applying the cleaning film after the leveling has been done, the cleaning film is not damaged by the leveling. This in turn improves the cleaning properties of the system.

According to one embodiment, the method may further comprise that the step of moving the measuring means to a place on the cleaning plate top area that is substantially above the adjustable attachment means used as a reference and measure a reference value with the measuring means, is repeated after each step of moving the measuring means to a place on the cleaning plate top area that is substantially above one of the two adjustable attachment means for adjusting the level and adjust that attachment means until the measuring means reads substantially the same as the reference value. The step of measuring a reference value that may be used to adjust and level the other corners of the cleaning plate may be done each time before adjusting any one of the corners of the cleaning plate. This may allow for a more accurate and less time consuming leveling.

According to one embodiment, the method may be part of manufacturing an integrated circuit, such as a chip or semiconductor. The integrated circuit may be part of any electronic device. The method may be used for manufacturing such an electronic device.

At least one embodiment of the method may be implemented using at least one embodiment of the system described above or any other system operable to implement an embodiment of the method. In certain embodiments, at least one embodiment of the method may be implemented partially in software embodied in computer-readable media.

In operation, the system is mounted in a probe machine. The operation system may be adopted to use the new system for cleaning a probe array at specific intervals. The operation system may be at least partially a computer implemented operating system.

The method and system improve die yield. The use of the described system and method has resulted in the percent of faulty detections made by a probe to be lowered. An increase of at least one percent in die yield is noted when the method and system is introduced in a probe machine.

The system discussed above may be used for cleaning probes when testing wafers and the method discussed above mounts such systems accurately within a probe machine for testing wafers. The invention, therefore, is well adapted to carry out the objects and attain the ends and advantages mentioned, as well as others inherent therein. While the invention has been described and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A system for cleaning probe contacts, comprising:
    a base plate comprising three openings for receiving each an adjustable attachment, and further openings for connecting the base plate to a probe machine; and
    a cleaning plate comprising on a bottom side three openings for receiving the respective adjustable attachment, and a top area for supporting a cleaning device, wherein the three openings in the cleaning plate do not reach into a top area of the cleaning plate;
    wherein the top area is between 60-100 mm times 75-100 mm, and the adjustable attachment devices allow the top area to be leveled by adjusting a distance between the cleaning plate and the base plate through the bottom of the cleaning plate.

2. The system according to claim 1, wherein
    each adjustable attachment comprises a screw and two nuts for each screw.

3. The system according to claim 2, wherein each opening in the cleaning plate is a blind threaded hole.

4. The system according to claim 3, wherein three screws are attached to the three blind threaded holes in the cleaning plate, respectively; each screw holding the base plate through each opening, respectively, with the two nuts on each side of the base plate.

5. The system according to claim 4, wherein one screw has a washer between the cleaning plate and base plate, for allowing adjustment space for the other two screws.

6. The system according to claim 2, wherein one screw is 10 mm longer than the other two.

7. The system according to claim 1, wherein the cleaning device is a cleaning film material or a tungsten carbide layer which can be attached to the top area of the cleaning plate.

8. The system according to claim 1, wherein the cleaning plate is 100 mm times 100 mm when mountable in a UF200 probe machine or the cleaning plate is 95 mm times 60 mm when mountable in an APM90 probe machine.

9. The system according to claim 1, wherein the system is arranged on a wafer chuck in a probe machine and is movable in the axial directions of the wafer chuck.

10. A method for mounting in a probe machine a system for cleaning of probe contacts, the system comprising:
   a base plate comprising three openings for receiving each an adjustable attachment, and further openings for connecting the base plate to a probe machine; and
   a cleaning plate comprising on a bottom side three openings for receiving the respective adjustable attachment, and a top area for supporting a cleaning device, wherein the openings in the cleaning plate do not reach into a top area of the cleaning plate;
   wherein the top area is between 60-100 mm times 75-100 mm, and the adjustable attachments allows the top area to be leveled,
   the method comprising the step of:
   coupling the base plate in the probe machine;
   coupling the cleaning plate to the base plate with the adjustable attachments by mounting one of the adjustable attachments as a reference, and mounting the two other adjustable attachments for adjusting the level of the cleaning plate; and
   leveling, with the aid of a measuring device for measuring distance held by the probe machine, the cleaning plate by repeating the following steps until the desired level is reached:
      moving the measuring device to a place on the cleaning plate top area that is substantially above the adjustable attachments used as a reference and measure a reference value with the measuring device;
      moving the measuring device to a place on the cleaning plate top area that is substantially above one of the two adjustable attachments for adjusting the level and adjust that attachments until the measuring means reads substantially the same as the reference value; and
      moving the measuring device to a place on the cleaning plate top area that is substantially above the other of the two adjustable attachments for adjusting the level and adjust that attachments until the measuring device reads substantially the same as the reference value.

11. The method according to claim 10, wherein each adjustable attachments comprises a screw and two nuts for each screw and the adjustments are made by turning the nuts.

12. The method according to claim 10, wherein the cleaning plate is mounted in a UF200 or an APM90 wafer probe machine.

13. The method according to claim 10, wherein the method further comprises the step of initially cooling the chuck to 30 degrees Celsius in the probe machine and allowing the machine to stabilize for 30 minutes.

14. The method according to claim 10, wherein the leveling is made to an accuracy of 5 μm.

15. The method according to claim 10, wherein the measuring means is a dial indicator.

16. The method according to claim 10, wherein a washer is placed on the screw used as reference point between the cleaning plate and the base plate.

17. The method according to claim 10, wherein the method further comprises, after the cleaning plate has been leveled, a step of applying a cleaning film to the cleaning plate.

18. The method according to claim 10, wherein the method further comprises that the step of moving the measuring device to a place on the cleaning plate top area that is substantially above the adjustable attachment used as a reference and measure a reference value with the measuring device, is repeated after each step of moving the measuring device to a place on the cleaning plate top area that is substantially above one of the two adjustable attachments for adjusting the level and adjust that attachments until the measuring device reads substantially the same as the reference value.

19. The method according to claim 10, wherein the mounting is part of manufacturing an integrated circuit or a semiconductor.

20. A system for cleaning probe contacts, comprising:
   a base plate comprising three mounting means for receiving each an adjustable attachment means, and means for connecting the base plate to a probe machine; and
   a cleaning plate comprising on a bottom side three holding means for receiving the respective adjustable attachment means, and a top area for supporting a cleaning means, wherein the holding means do not reach into a top area of the cleaning plate;
   wherein the adjustable attachment means allows the top area to be leveled by adjusting a distance between the cleaning plate and the base plate through the bottom of the cleaning plate.

* * * * *